(12) United States Patent
Chen et al.

(10) Patent No.: US 8,889,397 B2
(45) Date of Patent: Nov. 18, 2014

(54) NUCLEOTIDES FOR PREVENTION AND TREATMENT OF BACTERIAL AND FUNGAL PATHOLOGIES

(75) Inventors: Yin Chen, Pearland, TX (US); Xin Xing Tan, Manvel, TX (US)

(73) Assignee: Star Biologics, Inc., Houston, TX (US)

( * ) Notice: Subject to any disclaimer, the term of this patent is extended or adjusted under 35 U.S.C. 154(b) by 1358 days.

(21) Appl. No.: 10/574,254

(22) PCT Filed: Jun. 3, 2004

(86) PCT No.: PCT/US2004/017331
§ 371 (c)(1),
(2), (4) Date: Mar. 30, 2006

(87) PCT Pub. No.: WO2004/108840
PCT Pub. Date: Dec. 16, 2004

(65) Prior Publication Data
US 2007/0020635 A1      Jan. 25, 2007

Related U.S. Application Data

(63) Continuation of application No. 10/453,410, filed on Jun. 3, 2003, now abandoned, and a continuation of application No. 10/743,956, filed on Dec. 23, 2003, now abandoned, and a continuation of application No. 10/818,158, filed on Apr. 5, 2004, now abandoned, said application No. 10/743,956 is a continuation-in-part of application No. 10/453,410, filed on Jun. 3, 2003, now abandoned, said application No. 10/818,158 is a continuation-in-part of application No. 10/743,956, filed on Dec. 23, 2003, now abandoned.

(51) Int. Cl.
*C12N 15/74* (2006.01)
*C12N 7/00* (2006.01)
*C12N 1/20* (2006.01)
*C12N 1/00* (2006.01)
*C12Q 1/68* (2006.01)
*A61K 48/00* (2006.01)
*C12N 15/113* (2010.01)
*C12N 15/10* (2006.01)
*C12N 15/11* (2006.01)

(52) U.S. Cl.
CPC .......... *C12N 15/1034* (2013.01); *C12N 15/113* (2013.01); *C12N 2320/11* (2013.01); *C12N 2310/111* (2013.01); *C12N 2330/31* (2013.01); *C12N 2310/11* (2013.01); *C12N 15/74* (2013.01); *C12N 15/111* (2013.01)

USPC .............. 435/235.1; 435/6.16; 435/254.2; 435/471; 435/483; 435/325; 435/252.3; 514/44 R

(58) Field of Classification Search
None
See application file for complete search history.

(56) References Cited

U.S. PATENT DOCUMENTS

| | | | | |
|---|---|---|---|---|
| 5,436,141 | A * | 7/1995 | Miyata et al. | 435/91.1 |
| 6,562,570 | B1 * | 5/2003 | Rossi et al. | 435/6 |
| 6,673,611 | B2 * | 1/2004 | Thompson et al. | 435/455 |
| 7,022,828 | B2 * | 4/2006 | McSwiggen | 536/23.1 |
| 7,034,009 | B2 * | 4/2006 | Pavco et al. | 514/44 |
| 7,355,035 | B1 * | 4/2008 | Atkins et al. | 536/24.5 |
| 7,419,964 | B2 * | 9/2008 | Chen et al. | 514/44 |
| 2004/0248101 | A1 * | 12/2004 | Chen et al. | 435/6 |
| 2005/0136393 | A1 * | 6/2005 | Chen et al. | 435/4 |
| 2008/0206154 | A1 * | 8/2008 | Chen et al. | 424/44 |
| 2008/0312173 | A1 * | 12/2008 | Chen et al. | 514/44 |

FOREIGN PATENT DOCUMENTS

| | | | |
|---|---|---|---|
| JP | 2006526416 A6 | * | 11/2006 |
| WO | WO 00/22114 A1 | * | 4/2000 |
| WO | WO 01/25419 | * | 4/2001 |
| WO | WO 01/25419 A1 | * | 4/2001 |
| WO | WO 2004/108840 A2 | * | 12/2004 |
| WO | WO 2006/037127 A2 | * | 4/2006 |

OTHER PUBLICATIONS

Kusunoki et al, BBRC, 2003, 301:535-539.*
Mirochnitchenko et al, JBC, 1994, 269/4:2380-2383.*
Chen et al, Antisense & Nucleic Acid Drug Development, 2000, 10:415-422.*
Chen et al, Expert Opin. Biol. Ther., 2002, 2/4:443-445.*
Mohuczy et al, Hypertension, 1999, 33/part II:354-359.*
Chen, Expert Opin. Biol. Ther., Oct. 2002, 2/7:735-740.*

* cited by examiner

*Primary Examiner* — Nita M Minnifield
(74) *Attorney, Agent, or Firm* — Ramey & Browning, PLLC

(57) ABSTRACT

A selectively inducible, single-stranded DNA (ssDNA) expression library, a method for constructing a ssDNA expression library, a method for screening ssDNA using the expression library, and a method for identifying ssDNA molecules that alter expression of bacterial and fungal gene(s) related to cell growth and toxin production and secretion. The screening library is used to, among other things, identify ODNs effective in stopping cell growth, killing bacteria or fungi, or preventing bacteria and/or fungi from synthesizing and secreting their toxins, and/or to discover ODNs effective in eukaryotic (e.g., mammalian) cells for targeted alteration of gene function. The library is also useful for identifying ssDNAs or ODNs that are used as therapeutic agents for, for instance, providing a method for treatment of bacterial infections such as sepsis.

19 Claims, 10 Drawing Sheets

Figure 6
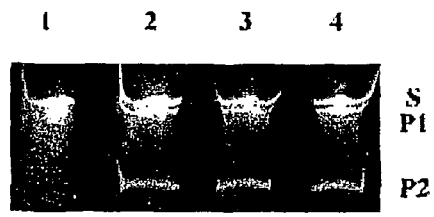
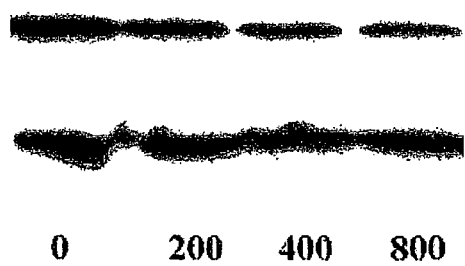
0    200    400    800
aTc (ng/ml)
Figure 8B
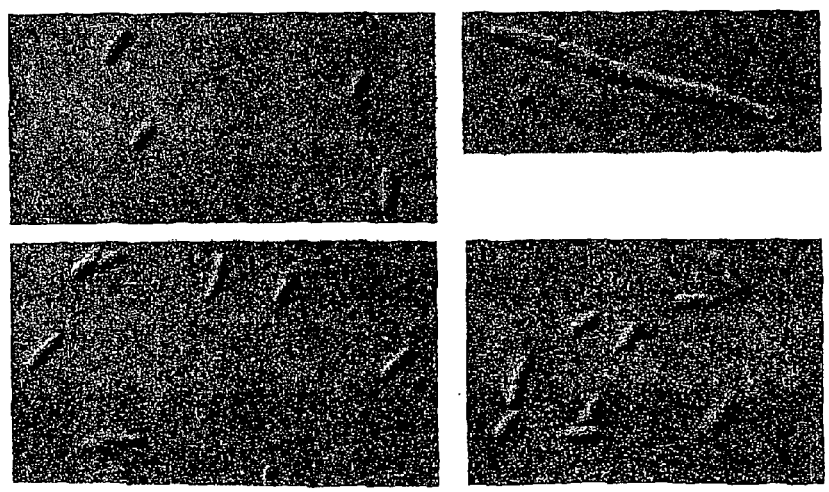

Figure 8A
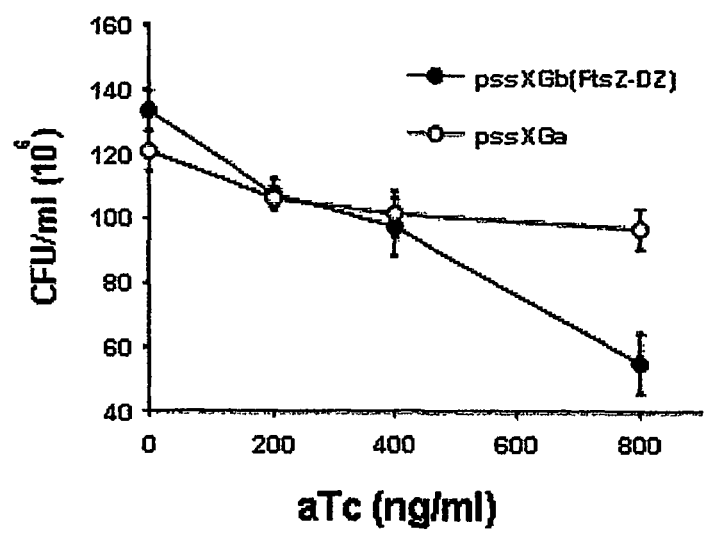
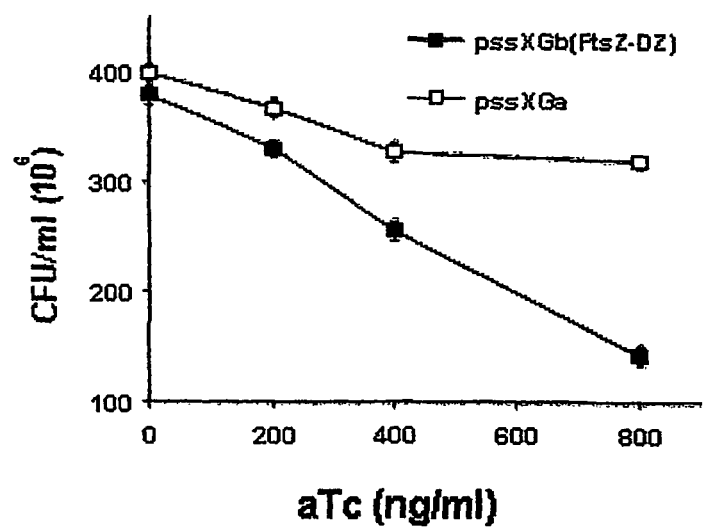

0ng/ml aTc    200ng/ml aTc

200ng/ml    0 ng/ml

0           200ng/ml pssxGb           CYGX080103

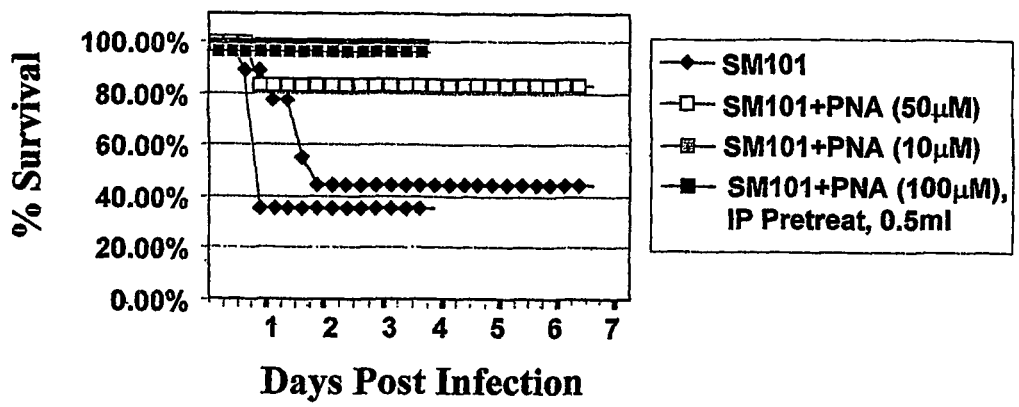
FIG. 12  Mouse survival after infection
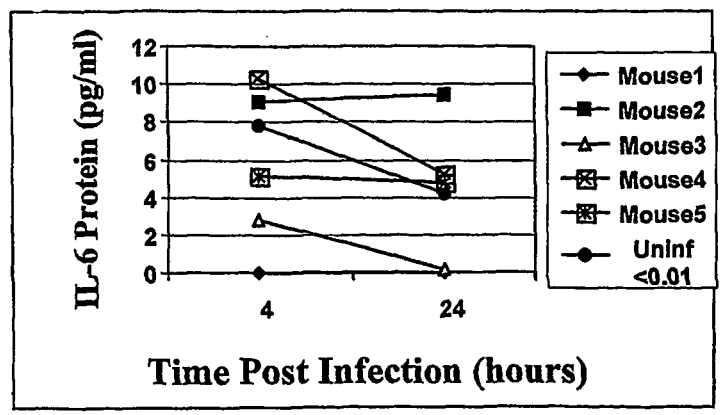
FIG. 13  Change in mouse serum IL-6 after infection FIG. 15 Inhibition of bacterial growth by ODN expression plasmid

NUCLEOTIDES FOR PREVENTION AND TREATMENT OF BACTERIAL AND FUNGAL PATHOLOGIES

Severe sepsis and septic shock are life threatening complications of infection and a common cause of death in intensive care units (Angus, et al., 2001, Crit. Care Med., 29: 1303-1310). Recent surveys estimate that severe sepsis accounts for 2-11% of all admissions to hospital or intensive care units (Mar et al., 2003, New Engl. J. Med., 348, 1546-1554) and the incidence is rising due to the aging of the population and increasing numbers of immunocompromised and critically ill patients. Sepsis comprises a complex clinical syndrome resulting from infection by bacterial and/or fungal pathogens (Cohen, 2002, Nature, 420, 885-891). Normally, an immunologic cascade ensures a protective response to microorganism challenge. However, a deficient defense may allow infection to become established or harm the host through maladaptive release of endogenous inflammatory compounds. This cascade of inflammation and coagulation fuels the progression of sepsis, resulting in hypoxia, ischemia, organ dysfunction, and ultimately death for a large number of patients. Additionally, diabetic individuals or others who suffer from lymphedema are at risk from opportunistic pathogens due to the growth potential afforded by the edematous medium or lack of circulation. Such infections may result in severe cellulitis or related sequelae that lead to sepsis.

Gram negative bacilli (mainly *Escherichia coli, Klebsiella* spp., and *Pseudomonas aeruginosa*) and Gram positive cocci (mainly staphylococci and streptococci) are common microbial pathogens isolated from patients with severe sepsis and septic shock (Bochud, 2001, Intensive Care Med., 27 (Suppl 1): S33-S48). Fungi, mostly *Candida*, account for about 5% of all cases of severe sepsis, but the incidence of fungal infections is increasing.

Gram negative infections occur in the lung, abdomen, bloodstream, or urinary tract. Endotoxins, in the form of lipopolysaccharides (LPS), are an important component of the outer membrane of gram negative bacteria and have a pivotal role in inducing gram negative sepsis (Alexander, et al., 2001, J. Endotoxin Res., 7:167-202). Gram positive bacteria are usually responsible for infections of skin, soft tissue, and intravascular devices, as well as primary bloodstream and respiratory infections. It is generally thought that the distinct cell wall substances of gram-positive bacteria and fungi trigger a similar cascade of events as gram negative bacteria, although the structures involved are not generally as well studied as gram-negative endotoxin. Gram positive bacteria can cause sepsis by at least two mechanisms: by producing exotoxins that act as superantigens and by components of their cell walls stimulating immune cel's (Calandra, 2001, J. Chemother., 13: 173-180). Gram positive bacteria without exotoxins can also induce shock, probably by stimulating innate immune responses through similar mechanisms to those in gram negative sepsis.

Numerous adjunctive treatments (other than antibiotics and supportive care) for severe sepsis and septic shock have been tested, including neutralization of microbial toxins and pro-inflammatory cytokines, non-specific anti-inflammatory and immunosuppressive drugs, and correction of abnormalities in coagulation. The results have been mixed (Vincent et al., 2002, Clin. Infect. Dis., 34: 1084-1093), and it does not appear that any one treatment addresses all sepsis conditions and/or causative agents.

While theoretical and experimental animal evidence exists supporting the use of large doses of corticosteroids in severe sepsis and septic shock, all randomized human studies found that corticosteroids do not prevent septic shock, reverse the shock state, or improve mortality. Lefering, et al., 1995, Crit. Care Med., 23, 1294-1303; Cronin, 1995, Crit. Care Med., 23, 1430-1439. Coagulation abnormalities are common in patients with sepsis and microvascular thrombosis. Treatment with activated protein C reduces mortality from severe sepsis (Bernard, et al., 2001, N. Engl. J. Med., 344: 699-709). So far as is known, it is the only drug to treat sepsis in the current market. However, treatment with this drug results in modest improvements in patient mortality at the price of a slight increase in bleeding events (Id.).

Prophylactic administration of antibiotics is, therefore, the treatment of choice for sepsis in hospitals (Cunha, 1995, Med. Clin. North Am., 79, 551-558). Antibiotics must be broad spectrum and cover gram-positive, gram-negative, and anaerobic bacteria because all classes of these organisms produce identical clinical presentations. Antibiotics must be administered parenterally in doses adequate to achieve bactericidal serum levels because clinical improvement correlates with the achievement of serum bactericidal levels rather than the number of antibiotics administered.

Unfortunately, many classes of antibiotics have become less effective as a result of antibiotic resistance by bacteria such as *S. aureus, S. pneumoniae* and *E. faecalis* (Nicolaou, et al., 2001, Scientific American, p. 56-61). Methicillin-resistant *S. aureus* (NMRA), penicillin-resistant *S. pneumococcus* and vancomycin-resistant *E. faecalis* (VRE) are now difficult to treat effectively (Pfaller, et al., 1998, Antimicrobial Agents and Chemotherapy, 42:1762-1770; Jones, et al., 1999, Microbiol. Infect. Dis., 33:101-112). Also alarming is the emergence of multi-drug resistance pathogens (Swartz, 1994, Proc Natl. Acad. Sci. USA, 91:2420-2427; Baquero, 1997, J. Antimicrobial Chemotherapy, 39:1-6). Fungal pathogens resistant to antifingal agents have also been documented and their frequency will likely increase (ex, 1997, Clin. Infect. Dis., 24:235-247).

The development of drug-resistant bacterial and fungal pathogens implicated in sepsis illustrates the need for a new approach to treatment of sepsis. On a broader scale, the emergence of drug-resistant pathogens illustrates the need for a new approach for the treatment of any pathological condition in which a bacterial or fungal agent is implicated. Infectious diseases such as tuberculosis, meningitis, and pneumonia, that would have been easily treated with antibiotics at one time, are no longer so readily thwarted.

The present invention therefore utilizes oligonucleotide-mediated intervention (OMI) technology to alter the activity of genes involved in such pathological conditions for therapeutic purposes. The ability to produce single strands of DNA (ssDNA) of any sequence and length in selected cells enables targeted alteration of gene expression at the genomic level using triplex-forming oligonucleotides (TFOs), at the messenger RNA (mRNA) level using antisense and DNA enzyme oligos, and at the protein level using ssDNA as aptamers (Chen, 2002, Expert Opin. Biol. Ther. 2(7) 735-740). Antisense, DNA enzyme, triplex, and aptamer technologies provide an efficient alternative to more difficult methods such as creating gene knockout in cells and organisms. Antisense oligonucleotides (ODNs) block gene expression by Watson-Crick base pairing between an ODN and its target mRNA (Crooke, 1999, Biochim. Biophys. Acta 1489:3144). Antisense ODNs have been used to effectively inhibit gene expression in eukaryotic cells and there is one antisense ODN-based product in the market and others in clinical trials (Uhlman, 2001, Expert Opinion Biol. Ther., 1:319-328). However, antisense technology is not used extensively in prokaryotic systems. Prokaryotic cells have themselves developed endogenous antisense mechanisms for gene regulation (Simons, et al., 1988, Ann. Rev. Genet., 22, 567-600). Earlier results indicated that gene expression in bacteria may be accessible to inhibition by modified ODNs (Jayayaraman, et al., 1981, PNAS, 78:1537-1541; Gasparro, et al., 1991, Antisense Res Dev., 1:117-140). Others reported that peptide nucleic acid (PNA) can inhibit gene expression in bacteria (Good, et al., 1998, Nature Biotechnology, 16:355-358). PNA, a DNA mimic in which the nucleotide bases are attached to a pseudopeptide backbone, hybridizes with complementary DNA, RNA, or PNA oligomers through Watson-Crick base pairing and helix formation.

One major factor in the efficacy of any OMI strategy is target site accessibility. Base composition can affect heteroduplex formation, but it does not appear to be the primary factor. There is now evidence that binding of complementary ODNs is determined by the secondary and tertiary structure of RNA molecules (Frauendorf, et al., Bioorg. Med. Chem. Lett., 1996, 4:1019-1024). Various approaches to identifying the accessible sites on target mRNAs in relation to antisense and/or DNA enzyme design have been developed. Conventionally, a linear shot-gun approach in which several ODNs, targeted to various regions of an mRNA, are synthesized and their antisense, DNA enzymatic or other activity (or binding affinity to the target sites) measured. However, only 2-5% of ODNs are generally found to be good antisense reagents. It is also known to use computer programs to select the target. For instance, the secondary structure of target RNA is predicted using an RNA folding program such as MFOLD (M. Zuker, 1989, Science, 244, 48-32) and antisense ODNs are designed to bind to regions that are predicted to be free from intramolecular base pairing. However, energy-based prediction methods of RNA structure are largely inadequate for designing antisense reagents and success using this approach has been limited.

Evidence that ribonuclease H (RNase H) is involved in antisense-mediated effects has led to the development of procedures for identifying accessible mRNA binding sites. In one procedure, RNase H is used with an ODN library comprising all possible ODNs of a defined length to identify accessible sites in mRNA For instance, for a length N, there are $N^4$ different possible ODNs comprising the ODN library set such that there are approximately $2.56 \times 10^6$ molecules for a 40-mer ODN. Library ODNs complementary to accessible sites on the target RNA produce hybrids with RNA that are identified as RNase H cleavage sites by gel electrophoresis and the library set members are tested to see which produces a down-regulating effect on a specific target mRNA Controlled expression systems such as the tetracycline regulatory system in prokaryotic cells allow selective gene down- or up-regulation, thereby supplying information on the gene product.

Hammerhead and hairpin ribozymes are catalytic RNA molecules that bind and cleave defined RNA targets that have been used to knock down gene expression of viral and cellular targets (see James, et al., Blood, 91:371-382, 1998). A method has been developed to identify accessible sites on ICP4 mRNAs for antisense-mediate-gene inhibition using a hammerhead ribozyme library that allows expression of the library components in mammalian cells (Pierce, et al., 1998, Nucleic Acid Research, 26:5093-5101). Although hammerhead ribozymes efficiently cleave specific mRNA L5 targets, their clinical application is limited because of instability caused by RNase degradation in vivo. Ribozyme libraries can also be used to identify genes involved in producing a particular phenotype. Researchers from Immusol, Inc. constructed a hairpin ribozyme library that was delivered to mammalian cells with plasmid or retroviral vectors (Welch, et al., Genomics, 66, 274-283, 2000, Li, et al., Nucleic Acid Research, 28:2605-2612, 2000, Kruger, et al., PNAS, 97:8566-8571, 2000, Beger, et al., PNAS, 98:130-135, 2001). By knocking down gene expression, they were able to identity novel genes or new functions of known genes. However, similar to hammerhead ribozymes, hairpin ribozymes have limited stability in vivo.

Ji, et al. constructed a library of 200 to 800 bp staphylococcal DNA fragments by shearing genomic DNA (Ji, et al., 2001, Science, 293:2266-2269). By transforming the library into S. aureus, random antisense RNA molecules were generated. Using this approach, genes were identified that could serve as targets for antibiotic discovery. A similar approach was used by Forsyth, et al. in S. aureus (Forsyth, et al., 2002, Molecular Microbiology, 43:1387-1400). However, this approach can only be used go for the identification of essential genes since antisense RNA with the size between 200-800 bp is not useful for therapeutic purposes because of 1) the instability of PNA molecules; 2) the difficult of synthesizing RNA molecules with the size of 200-800 bp; and 3) the problem of delivering RNA to appropriate cells.

There is, therefore, an emergent demand for the discovery and development of new therapeutics against bacterial and fungal pathogens. Recent advances in DNA sequencing technology have made it possible to elucidate the entire genome sequences of pathogenic bacteria. Genomic sequencing reveals all of the information in bacteria related to potential targets by antibiotics and therefore provides a more rational target-based approach to the development of new therapeutic agents. Thus, the use of a screening library to identify ODNs for inhibiting growth of bacteria and/or fungi, killing bacteria and/or fungi, or preventing bacteria and/or fingi from synthesizing and secreting toxins is one focus of the present invention. Use of the screening library to discover ODNs effective in eukaryotic (e.g., mammalian) cells for targeted alteration of gene function is a logical application.

It is, therefore, an object of the present invention to provide a method for identifying ssDNAs such as triplex forming oligos (TFOs), antisense oligos, DNA enzymes, or aptamers useful as therapeutic antibacterial and/or antifungal agents.

An additional object of the present invention is to provide a method for identifying bacterial and/or fungal genes that can serve as targets for discovery of antibacterial and/or antifungal agents.

An additional object of the present invention is the provision of a method, and ODNs, for treating bacterial and fungal infections.

An additional object of present invention is to provide a method for regulating gene expression in eukaryotic cells in a controlled manner using a selectively-inducible expression vector such as the tetracycline system.

Yet another object of the present invention is to identify genes necessary for bacterial and fungal viability and host genes associated with the exaggerated innate immune response indicative of sepsis.

An additional object of the present invention is to provide ODNs, and their sequences, that knock down (silence) bacterial, fungal, and host genes.

An additional object of the present invention is to provide ODNs, and their sequences, as therapeutic antibacterial and antifungal agents.

An additional object of the present invention is to provide means for delivery of therapeutic ODNs into target bacterial or fungal cells.

An additional object of the present invention is to provide plasmid constructions that are used to knock down bacterial, fungal, and host genes.

An additional object of the present invention is to provide plasmid constructions that are used as therapeutic antibacterial and antifungal agents.

Still another object of the present invention is to provide a treatment for a bacterial and/or fungal infection such as sepsis in an animal patient comprising the steps of contacting a bacterial or fungal causative agent with an ODN comprising a sequence targeted to a specific gene of the causative agent for altering the expression of the specific gene to inhibit growth of the causative agent, kill the causative agent, or inhibit the synthesis or secretion of toxin by the causative agent.

These objects, and many others, are met by providing, a selectively-inducible single-stranded DNA (ssDNA) expression library, a method for constructing the ssDNA expression library, a method for screening a ssDNA expression library, and a method for identifying ssDNA molecules that switch bacterial gene(s) related to cell growth, replication, and/or toxin production and secretion on or off. The method comprises a method for constructing a set of randomly ordered, fixed length oligodeoxynucleotide (ODN) strands and subcloning these ODNs into expression vectors constituted so that, when transformed into cells that are subsequently exposed to certain chemical environments, the cell reacts by expressing the individual ODN sequence programmed into the expression vector. Cells containing instructions for an individual ODN are grown into colonies and each colony is divided into control and experimental sets. When an experimental colony is exposed to the chemical inducing production of an ODN, the ODN is expressed and putatively alters cellular gene function, for instance, protein production, producing a different cell phenotype. If the phenotypic expression represents a desired end result, the control colony is treated to extract the DNA to determine the exact nucleotide sequence of the ODN that produced the phenotype in question.

This method is used to identify ODNs that inhibit the growth of, kill, or inhibit the synthesis of secretion of toxins by bacteria and/or fungi, thereby making it possible to identify new therapeutic agents against pathogenic bacteria and/or fingi and to identify essential genes of the bacteria and/or fungus that can serve as additional targets for discovery of new therapeutic agents. The same methods and screening library are utilized to identify ssDNA molecules that switch bacterial and fungal gene(s) related to cell growth, replication, and/or toxin production and secretion on and/or off.

The present invention comprises methods for treatment of bacterially- or fungally-induced diseases such as sepsis by producing ODNs in bacterial or fungal cells in vivo so that, when said ODNs reach and knock down their target genes, and thereby kill bacterial or fungal cells or inhibit their growth, the bacterial or fungal accumulation in the bloodstream is held constant or diminished and the sepsis syndrome is reduced or eliminated.

In another aspect, the present invention provides a novel ssDNA enzyme having a catalytic sequence flanked by targeting sequences that are effective in killing bacterial or fungal cells into which the sequence is introduced and/or in which the is sequence is synthesized in vivo.

The present invention also comprises a method for treatment of sepsis in which ODNs are produced in host cells in vivo so that, when the ODNs silence their target genes, the host exaggerated innate immune response is abrogated and the sepsis syndrome is relieved.

The present invention also comprises a method for treatment of sepsis by delivering ODN-expressing plasmid constructions into host cells in vivo so that, when the ODNs are produced intracellularly and knock down their target genes, the host exaggerated innate immune response is abrogated and the sepsis syndrome is relieved.

In another aspect, the present invention also comprises a kit including an oligonucleotide targeted to a gene in a microbial pathogen such as bacteria or fungi that operates to downregulate or otherwise alter the expression of the gene to kill the bacterial or fungal cells or inhibit their growth, or to decrease the synthesis or secretion of a toxin by the bacterial or fungal cell and a pharmaceutically acceptable excipient for use in treating a bacterial or fungal pathological condition.

Referring now to the figures, FIG. 1 is a schematic representation of the plasmid pssXG constructed in accordance with the present invention and showing the content and organization of the biochemical instructions, in this instance, in the form of a loop of double-stranded DNA that is introduced into a target bacterial cell, to cause the target cell to produce certain desired nucleic acids as described infra.

FIG. 2 shows the plasmid pssXG of FIG. 1 as modified to produce an FtsZ gene-targeted DNA enzyme in a target cell, and designated pssXGb(FtsZ-DZ).

A critical component of the plasmid pssXGb(FtsZ-DZ) shown in FIG. 2 is the reverse transcriptase enzyme, and FIG. 3 shows the results of a western blot assay for expression of HIS-tagged reverse transcriptase MT) induced by tetracycline in *E. coli*. Bacterial cells carrying pssXGb(FtsZ-DZ) vector were grown at 37° C. in the presence of 0, 100, or 200 ng/ml aTc for 1 hour (lanes 1-3), 2 hours (lanes 4-6), or 3 hours (lanes 7-9). Cell lysates were used for the assay and the RT bands are marked with an arrow, confirming the activity of the RT enzyme.

FIG. 4 shows the results of a second assay for verifying the expression and activity of the reverse transcriptase (RT) in the pssXGb(FtsZ-DZ) plasmid shown in FIG. 2. In this assay, production of HIS-tagged RT in *E. coli* was induced by tetracycline. Bacterial cells carrying vector were grown at 37° C. until OD 280 value of 0.5 and then 200 ng/ml of aTc, a derivative of tetracycline, was added to the cells and incubated for another 1-2 hours. Cell lysates were used for the assay, conducted in accordance with Silver, et al. (1993, Nucleic Acids Res. 21: 3593-3594). Lane 1: without tetracycline induction; Lane 2: one hour aTc induction; Lane 3: two hour aTc induction. PCR amplification product is marked by an arrow.

FIG. 5A shows the predicted structure of the mRNA produced by the FtsZ gene (Tetart, et al., 1992, Mol. Microbiol. 6: 615-620). The arrow indicates a loop at which the nucleic acids do not match up, thereby creating an opportunity for a single-stranded nucleic acid sequence to bind to the mRNA. As set out below, the GU site at position 880 indicated by the arrow was exploited in designing an FtsZ mRNA-cleaving DNA enzyme. FIG. 5B shows the design of this FtsZ mRNA-cleaving DNA enzyme (the 3' to 5' sequence) and its targeting sequence, or substrate (the 5' to 3' sequence), respectively.

FIG. 6 shows the results of in vitro cleavage of FtsZ RNA and verifies that the DNA enzyme of the present invention functions to digest the target mRNA. Lane 1 is a control reaction incubated for 2 hrs in the absence of DNA enzyme. S: substrate; P1 (857 nt) and P2 (368 nt): DNA enzyme digestion products.

FIG. 7 shows the results of an assay using an antibody specific for FtsZ protein for detection of that protein in cells in which the pssXG and pssXGb(FtsZ) plasmids have been introduced when induced for the purpose of demonstrating DNA enzyme-mediated repression of ftsZ gene expression: A. bacterial cells carrying the pssXGb(FtsZ-DZ) vector; B. bacterial cells carrying the control pssXGa vector. As set out below, an inducible system was utilized to facilitate screening.

FIG. 8A shows the inhibition of cell proliferation by the in vivo expressed FtsZ mRNA-cleaving DNA enzyme of the present invention.

FIG. 8B shows the morphology of bacterial cells carrying pssXGb(FtsZ-DZ): k bacterial cells carrying pssXGb(FtsZ-DZ), without aTc; B. bacterial cells carrying pssXGb(FtsZ-DZ), with 800 ng/ml aTc; C. bacterial cells carrying vector pssXGa, without aTc; and D. bacterial cells carrying pssXGa, with 800 ng/ml. The long filamentous cell (B) is indicative of a cell that cannot divide.

FIG. 9 shows the result of library screening. Colonies were grown in duplicate in LB plates with or without aTc. Positive clone (containing the pssXGb vector including the sequence CYGX080103) is marked by an arrow.

FIG. 10 shows the re-confirmation the inhibitory effect of the positive clone (CYGX080103, FIG. 9) from library screening. The CYGX080103 plasmid and the plasmid without ODN insert as negative control were transformed into DH5αPro and plated onto LB media with or without 200 ng/ml aTc. FIG. 10A shows that DH5αPro carrying the CYGX080103 plasmid grows normally on media without aTc, but not on media with aTc. DH5αPro carrying plasmid without the ODN insert grows on both media (FIG. 10B).

FIG. 11 shows the results of transformation of ODN (CYGX080103) expression vector into *E. coli* Xl10-gold (kan) cells. The transformants were plated on LB media with chloramphenicol and incubated at 37° C. O/N. No XL10-gold (kan) cells carrying CYGX080103 expression plasmid grew on the LB media but the XL10-gold(kan) cells carrying the plasmid without the ODN insert grew normally.

FIG. 12 shows survival of infected mice with or without ODN treatment. The log-phase preparation of bacteria was diluted in PBS, and $3\times10^8$ CFU of bacteria was i.p. injected to induce mouse sepsis. To treat mice, the ODN was either mixed with bacteria in vitro and then injected or mice were pretreated by ODN before infection. Serum was gathered and proinflammatory cytokines (IL-6, TNF, IL-1) and bacterial load tested and mouse behavior monitored at various time points after injection.

FIG. 13 shows changes in mouse proinflammatory cytokine IL-6 4 and 24 hr after bacterial infection; IL-6 concentration was measured using a commercial kit.

FIG. 14 shows bacterial growth inhibition by ODN. Immediately after diluting the O/N cultures 1/50, ODN was added to final concentrations of 4 uM, 40 μM or 400 μM with equal volume water as a negative control, and incubated with shaking at 30° C. After 2, 4 or 6 h, the growth was measured by viable cell count, which was done by diluting the cultures and plating on LB plates with streptomycin.

The methods and constructs of the present invention are better understood by reference to the following description of several embodiments thereof.

Construction of Tetracycline-Inducible Prokaryotic ssDNA Expression Vector.

Figure 1:
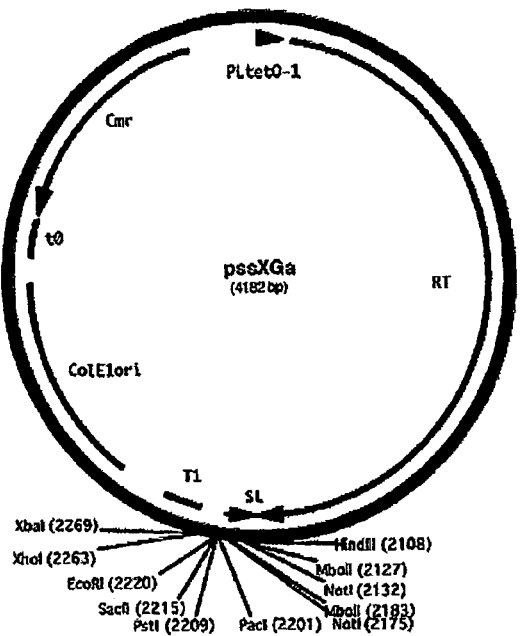

PCR amplification was carried out using the eukaryotic plasmid pssXE, described in International Application No. PCT/US00/27381, which application is hereby incorporated into this specification in its entirety by this specific reference, as the template. DNA primers used in the PCR reaction, 5'NheIPvuIATG 5'-CTAGCTAGCTAGCGATCGATGGGACCAATGG [Seq. ID No. 1]
GGCAG-3'
and 3'KpnI
5'-CGGGGTACCAGTATTCCCTGGTC-3'    [Seq. ID No. 2]

were synthesized by Integrated DNA Technologies (Coralville, Iowa). The PCR amplified DNA fragment was double-digested with NheI and KpnI and then subcloned into the pssXE vector that was double-digested with the same enzymes. The replacement removes the sequence before the translation starting site (ATG), which is unnecessary for prokaryotic gene expression, while creating a new restriction enzyme site, PvuI. The newly created construct was digested with PvuI and XbaI. The PvuI-XbaI fragment contains all the essential elements for ssDNA production, including:

1) Mouse Moloney leukemia viral reverse transcriptase (Mo-MuLV RT) gene coding for a truncated but fully active RT (Tanase, et al., PNAS, 2000, 85:1777-1781);
2) primer binding site (PBS) along with some flanking regions of the promoter that are essential for the reverse transcription initiation by MoMuLV RT (Shinnick, et al., Nature, 1981, 293:543-548); and 3) stem-loop structure designed for the termination of the reverse transcription reaction all as described in the above-incorporated International Application No. PCT/US00/27381. This DNA fragment was subcloned into the pPROTet.E 233 vector (BD Bioscience, Palo Alto, Calif.) and the newly created construct was designated as pssXGa, shown in FIG. 1. However, the sequent of bacteria tRNAPro is different from mammalian tRNAPro, which was desired to bind with the PBS in mammalian cells. Because bacterial tRNAVal can be utilized as primer for RT, a new PBS was designed to replace the PBS used in the vector pssXE that is used for mammalian cells. The sequence of the novel PBS is 5'-TGGTGCGTCCGAG-3'.    [Seq. ID No. 3]

Figure 2:
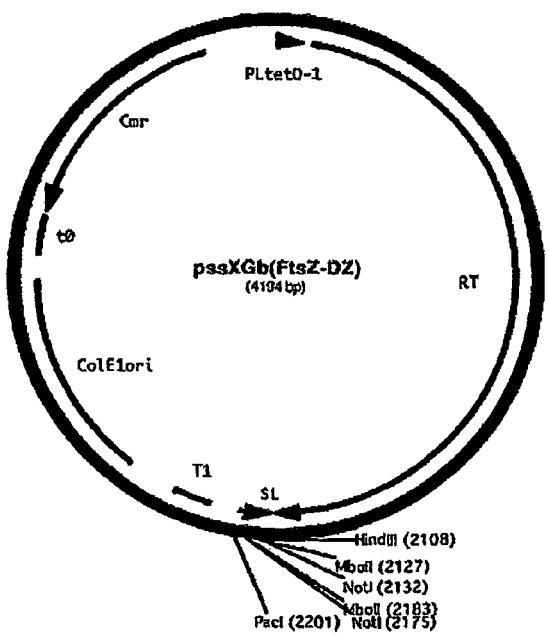
Figure 3:
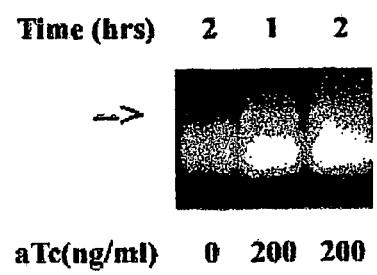
Figure 4:
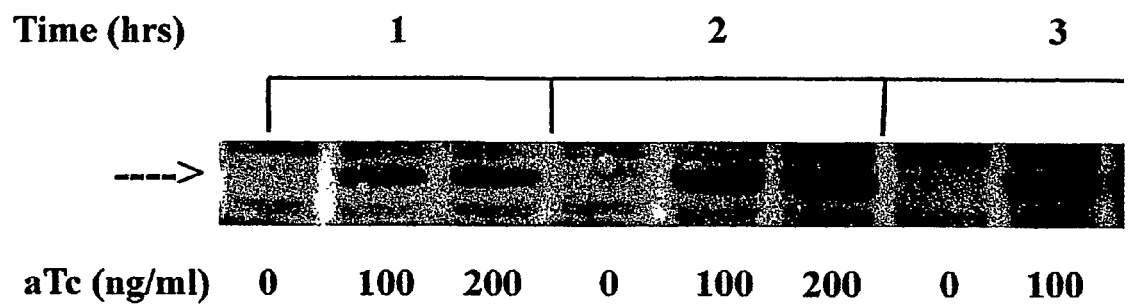

To construct a vector expressing the desired DNA enzyme and replace the original primer binding site (PBS) in the expression cassette of pssXE(CMV), the ODNs of sequence 5'-dTAACTGGATGATCGTTGTAGCTAGCCTTCG [Seq. ID No. 4]
AAACTTGGTGGTGCGTCCGAGTGGACCGGGAGAC
CCCTGCTCGAGT-3'
and 5'-CTAGACTCGAGCAGGGGTCTCCCGGTCCACT [Seq. ID No. 5]
CGGACGCACCACCAAGTTTCGAAGGCTAGCTACA
ACGATCATCCAGTTAAT-3' were annealed to produce a synthetic duplex with 5'PacI and 3'XbaI cohesive ends and ligated into the PacI and XbaI sites of pssXGa. The resulting vector was designated pssXGb (FtsZ-DZ) and is shown in FIG. 2.

pPROTet.E233 is a tetracycline-inducible bacterial expression vector expressing fusion protein with 6×HN. It utilizes the $P_{Ltet}$O1 promotor, which is tightly repressed by the highly specific Tet repressor protein and induced in response to anhydrotetracycline (aTc), allowing control of induction over a wide range (anhydrotetracycline is a derivative of tetracycline that acts as a potent inducer of PROTet.E Systems). The pssXG vector was transformed into the bacterial strain DH5αPro (BD Bioscience, Palo Alto, Calif.) in the presence of 34 µg/ml choloramphenicol (Cm) and 50 µg/ml spectinomycin (spec). Spectinomycin is used to select for DH5αPro cells that carry transcription units encoding TetR (Lutz, et al., Nucleic Acids Res., 1997, 25:1203-1210) The DH5αPro cells express defined amounts of the Tet repressors. Cell lysates were prepared using B-PER II Bacterial Protein Extraction Reagent (Pierce, Rockford, Ill.) according to manufacturer's instruction. Using cell lysates, expression of reverse transcriptase (RT) was confirmed by RT activity assay using cell lysates according to Silver, et al. (Nucleic Acids Res., 1993, 21:3593-3594) as shown in FIG. 3 and with western blot using antibody against 6xHN (BD Bioscience, Palo Alto; CA) as shown in FIG. 4.

Inhibition of Bacterial Growth By DNA Enzyme Targeted To FtsZ

Cell division is critical for bacterial survival; bacteria such as *E. coli* normally divide by binary fission, producing two daughter cells of equal size, each containing a nucleoid. FtsZ is an essential gene for bacterial division and viability. Division starts with localization of FtsZ to the center of the mother cell and formation of a septal structure, the Z ring, and other essential cell division proteins are then recruited to the Z ring. Deletion and mutation of the FtsZ gene blocks cell division at an early stage and therefore presents a target of opportunity for a new therapeutic agent against a broad range of bacterial pathogens.

Figure 5:
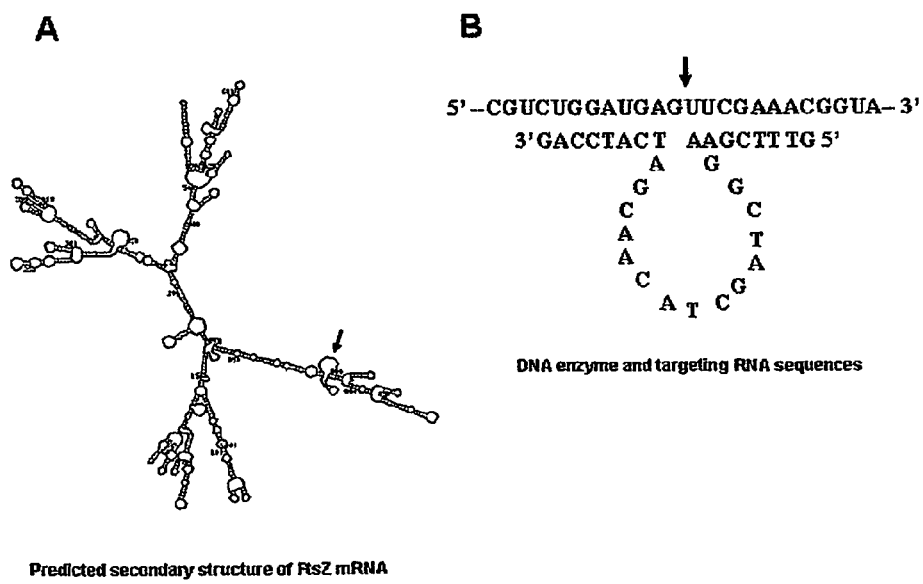

Because of their ability to bind and cleave any target RNA at purine/pyrimidine junctions, DNA enzymes are capable of interfering with gene expression as described in the above-incorporated International Application No. PCT/US00/27381. Based on the predicted secondary structure of FtsZ mRNA, DNA enzymes (DNAzymes) were designed for targeting various sites on this mRNA including, for instance, the loops at positions 50-66, 530-547, 612-629, 648-662, 871-887, 958-972, and 1032-1048. Specifically, 10-23 DNA enzyme cleavage sites are plentiful in most biological substrates and thus provide the opportunity to achieve maximum cleavage efficiency, and a 10-23 DNA enzyme targeted against the GU site at position 880 was designed with the following 31 nt sequence:

[Seq. ID No. 6]
5'-GTTTCGAAGGCTAGCTACAACGATCATCCAG-3' with a predicted free energy 21.3 kcal/mol (FIG. 5). It will be apparent from FIG. 5 that this 31 nt enzyme is comprised of a 15 nucleotide catalytic domain flanked by random target-binding domains of eight nucleotides, but those skilled in the art who have the benefit of this disclosure will recognize that the target-binding domains may vary in size from as few as three nucleotides up to as many as 25 or more nucleotides. In a preferred embodiment, the target-binding domains are comprised of seven to ten nucleotides such that the enzyme takes the form 5'-$N_1$-GGCTAGCTACAACGA-$N_2$-3'   [Seq. ID No. 7]

where $N_1$ and $N_2$ represent any sequence of nucleotides that target a specific RNA ranging in size from 3 to 25 nucleotides, and preferably seven to ten nucleotides:

The ability of the pssXGb(FtsZ-DZ) expression vector of the present invention to produce DNA enzyme molecules in bacterial cells was tested by evaluating the cleavage activity of the designed DNA enzyme in a cell-free system. The 1225 nt FtsZ RNA, produced by in vitro transcription, is used as a substrate and the cleavage assay is carried out at 37° C. for various period of time as indicated in a 10 µl reaction containing 10 mM $MgCl_2$, 50 mM Tris-HCl, pH 7.5, 100 nM template FtsZ RNA, 100 µM DNA enzyme, and 10 units RNasin. As shown in FIG. 6, the synthetic DNA enzyme can effectively cleave the FtsZ RNA in as short a time as 0.5 hr, producing the products with expected sizes (368 nt and 857 nt).

Other DNA enzymes have been designed to target the loops of the FtsZ mRNA other than at position 880 as listed above. For instance, a DNAzyme was designed for targeting the loop at position 1032-1038 with the following sequence:

[Seq. ID No. 8]
5'-CCTGCTTAGGCTAGCTACAACGATGGTCACC-3'.

Given that the designed DNA enzyme has been shown capable of cleaving FtsZ RNA in vitro (FIG. 6) and an aTc regulated expression vector can produce active RT (FIGS. 3 and 4), the expression vector is used to generate the DNA enzyme in cells and the effects of the DNA enzyme on the expression of the FtsZ gene is then determined. As shown in FIG. 7, bacterial cells carrying the pssXGb(FtsZ-DZ) vector (A) as well as negative control cells carrying the pssXGa vector (B) may be grown in the presence of various amount of aTc (0, 200, 400, 800 ng/ml) for 3 hrs. Compared to the cells grown in the absence of aTc, the FtsZ expression level in the bacterial cells carrying pssXGb(FtsZ-DZ) is reduced significantly upon addition of aTc (FIG. 7A). This reduction is not observed in the control cells (FIG. 7B).

Because FtsZ gene is essential for bacterial division and viability and FIG. 7 indicates that the intracellularly-generated DNA enzyme significantly represses FtsZ expression, the effect of the expressed DNA on bacterial cell proliferation was investigated. Bacterial cells carrying the pssXGb(FtsZ-DZ) vector were grown in the presence of various amounts of aTc (0, 200, 400, 800 ng/ml) for either 1 or 2 hrs and viable cells were enumerated. As shown in FIG. 8A, cell growth was inhibited in time and aTc-concentration dependent manner. Furthermore, long filamentous cells were observed to be formed as a result of the cell growth inhibition (FIG. 8B).

Construction of a Tetracycline-Inducible ssDNA or ODN Expression Library.

Library inserts were generated by annealing three ODNs, CY(SacII)-40,

| | |
|---|---|
| CTCTCACTCC(N)40ACTGTTGAAAGGC | [Seq. ID No. 9] |
| CY(SacII)-L, CGGAGAGTGAGG and | [Seq. ID No. 10] |
| CY(SacII)-R, CTTTCAACAGT | [Seq. ID No. 11] | at the molar ratio of 1:20:20. "N" represents any base A, T, C, or G. There are thus 40-mer sequences randomly synthesized and represented as CY(SacII)-40 ODNs. The ODNs were mixed and denatured at 95° C. for 3 min and then cooled slowly to room temperature over approximately 1 hr. Since CY(SacII)-L complements the left arm of CY(SacII)-40, while CY(SacII)-R complements the right arm of the same ODN, partial double-stranded ODNs are formed by the annealing process. The annealed ODN formed a partial double-stranded DNA and was filled in those remaining single-stranded Ns and blunt ended using the DNA Polymerase I, Large (Klenow) Fragment New England Biolabs, Beverly, Mass.). The double-stranded DNA was then subcloned into the prokaryotic ssDNA expression vector pssXGb and transformed into DH5αPRO cells by electroporation.

```
DNA enzyme expression library is constructed
similarly using a. DZlib1
5'-CTCGAGTCTAGANNNNNNNNGGCTAGCTACA [Seq. ID No. 12]
ACGANNNNNNNNTTAATTAAGCTAGC-3'

(N can be either A or T, or C or G) and
b. DZlib2
5'-GCTAGCTTAATTAA-3'.            [Seq. ID No. 13]
```

The two oligonucleotides are mixed at a molar ratio of 1:20 (a:b) and annealed to form a partial double-stranded DNA by heating for 5 min at 75° C., then cooled slowly to room temperature. The recessed 3' termini of the partial double-stranded DNA was filled by Klenow fragment, and the resulting double-stranded DNA digested with PacI and XbaI. The double digested products were then gel purified. After phenol extraction and ethanol precipitation, the PacI/XbaI digested, library DNA was cloned into the pssXGb expression vector. ssDNA Expression Library Screening.

Figure 9:

Since the ssDNA expression library was constructed based on a tetracycline inducible vector, bacterial cells containing the ssDNA expression library were plated in duplicate in Luria broth (LB) plates in the presence or absence 200 ng/ml aTc. Colonies growing only in the absence of aTc, as shown in FIG. 9, were identified as positive colonies. Plasmid DNA was extracted from the positive colony from the library screening, and the insert sequences determined by 3' end single-pass sequencing. The insert generated by this set of experiments was named CYGX080103, with sequence of:

```
5'-CTTTCAACAGTTTTGATGACCTTTGCTGACC [Seq. ID No. 14]
ATACAATTGCGATATCGTGGGAGTGAGAG-3'.
```

The sequence was then analyzed using GenBank BLASTN program to identify the potential gene targets based on sequence homologies. The ODNs comprised in the CYGX080103 and their potential genes that can be knocked down in accordance with the present invention include, but are not limited to,

```
CYGX08010301
5'-CCTTTGCTGACCATAC-3'         [Seq. ID No. 15]
and its target btuE (GenBank ID: NP-416225.1), CYGX08010302
5'-GACCTTTGCTGACCA-3'          [Seq. ID No. 16]
and its target CaiB (GenBank ID: NP-414580.1), CYGX08010303
5'-ACAGTTTTGATGAC-3'           [Seq. ID No. 17]
and its target ydgD (GenBank ID: NP-418152.1), CYGX08010304
5'-ACAATTGCGATAT-3'            [Seq. ID No. 18]
and its target ygcQ (GenBank ID: NP-417249.2), CYGX08010305
5'-GACCTTTGCTGAC-3'            [Seq. ID No. 19]
and its target ftsH (GenBank ID: NP-417645.1), CYGX08010306
5'-TCAACAGTTTTGATGAC-3'        [Seq. ID No. 20]
and its target ppiB (GenBank ID: NP-415058.1), CYGX08010307
5'-ATGACCTTTGCTG-3'            [Seq. ID No. 21]
and its target yihI (GenBank ID: NP-418308.1), CYGX08010308
5'-CAGTTTTGATGA-3'             [Seq. ID No. 22]
and its target zntA (GenBank ID: NP-417926.1), CYGX08010309
5'-ACCTTTGCTGAC-3'             [Seq. ID No. 23]
and its target yicI (GenBank ID: NP-418116.1), CYGX08010310
5'-TTGCTGACCATA-3'             [Seq. ID No. 24]
and its target fhuA (GenBank ID: NP-414692.1), CYGX08010311
5'-TGACCTTTGCTG-3'             [Seq. ID No. 25]
and its target rplD (GenBank ID: NP-417778.1), CYGX08010312
5'-GTTTTGATGACC-3'             [Seq. ID No. 26]
and its target ilvB (GenBank ID: NP-418127.1), CYGX08010313
5'-GCGATATCGTGG-3'             [Seq. ID No. 27]
and its target lepB (GenBank ID: NP-417063.1), CYGX08010314
5'-TTGATGACCTTT-3'             [Seq. ID No. 28]
and its target aroK (GenBank ID: NP-417849.1), CYGX08010315
5'-TGGGGAGTGAG-3'              [Seq. ID No. 29]
and its target mfd (GenBank ID: NP-415632.1), CYGX08010316
5'-TTGCTGACCAT-3'              [Seq. ID No. 30]
and its target rlpA (GenBank ID: NP-415166.1), CYGX08010317
5'-TTTTGATGACC-3'              [Seq. ID No. 31]
and its target accA (GenBank ID: NP-414727.1), CYGX08010318
5'-TGATGACCTTT-3'              [Seq. ID No. 32]
and its target pgpA (GenBank ID: NP-414952.1).
```

Figure 10A:
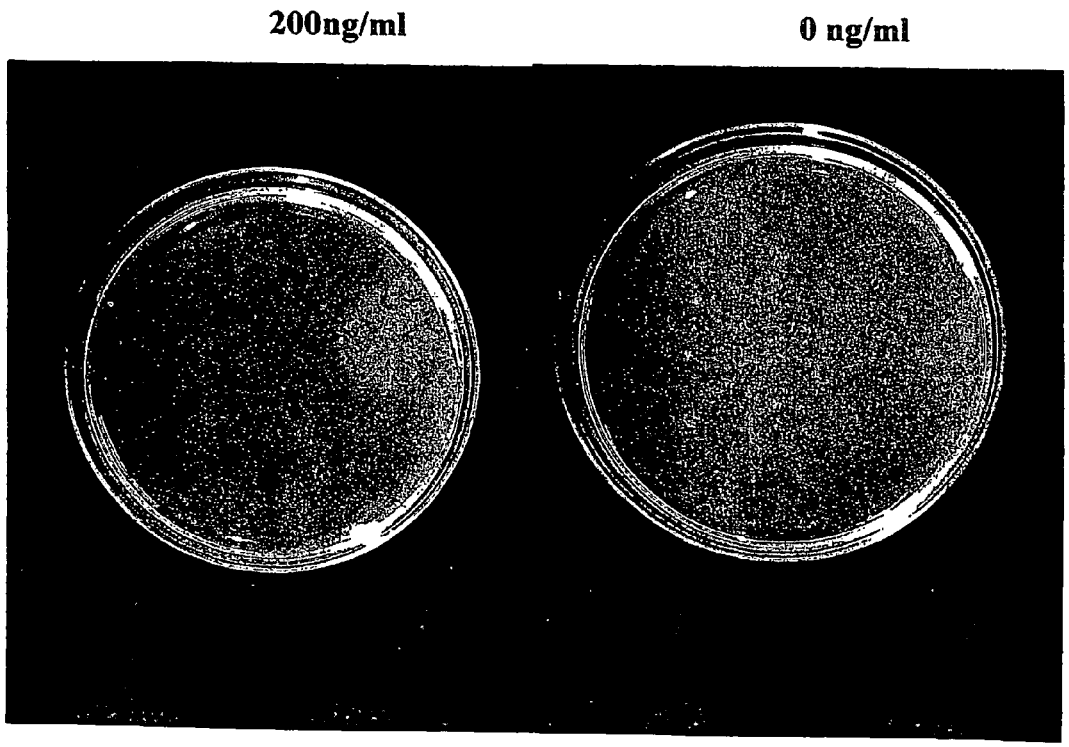
Figure 10B:
Figure 11:

The antibacterial efficacy of the ODN CYGX080103 was further evaluated in two separate experiments. The first was designed to examine the conditionally lethal effect of the ODN expression plasmid in the host cell DH5αPro, the bacterial strain employed in the library screening. The second experiment was designed to study the effect of the ODN expression plasmid on other bacterial strains. In the first study, the ODN expression plasmid and the plasmid without ODN insert as negative control were transformed into DH5αPro and plated onto LB media with or without 200 ng/ml aTc. As shown in FIG. 10A, DH5αPro cells carrying the ODN expression plasmid grow normally on the media without aTc but not on media with aTc. DH5αPro cells carrying the plasmid without the ODN insert grow on both media (FIG. 10B). In the second study, the ODN expression plasmid and the plasmid without ODN insert were transformed into E. coli XL10-gold(kan). The resulted transformants were plated on LB media with chloramphenicol and incubated at 37° C. O/N. As shown in FIG. 11, no XL10-gold(kan) carrying ODN expression plasmid grew on the LB media, while the XL10-gold(kan) carrying the plasmid without the ODN insert grew normally.

Development of a Mouse Sepsis Model.

E. coli SM101, a temperature-sensitive UDP-N-acetylglucosamine acyltransferase mutant that loses all detectable acyltransferase activity, and its wild-type K12, were i.p. injected as described below to induce sepsis in mice. SM101 has a defect in lipid A biosynthesis that causes the outer membrane to be permeable to high-molecular-weight substances. The lipid A content of SM101 is reduced 2-3-fold compared with the wild-type. To prepare the bacteria for mouse infection, log-phase cultures of SM101 were grown in LB medium at 37° C. to an optical density at 600 nm of 1.1 (equivalent to $5 \times 10^8$ CFU/ml), followed by centrifugation and resuspension in sterile phosphate-buffered saline (PBS) at 4° C. This log-phase preparation of bacteria was serially diluted in PBS, and $3 \times 10^8$ CFU of bacteria was i.p. injected to induce mouse sepsis. Serum was gathered and pro-inflammatory cytokines (IL-6, TNF, IL-1) and bacterial load tested, and mouse behavior monitored, at various time points after injection. All mice bled at every 24 hours. At 6 hours, mice showed evidence of infection (lethargy, warm to the touch, scruffy). As shown in FIG. 12, around 60% mice died within 48 hours after infection. As shown in FIG. 13, 3 of 5 mice showed significant decrease in serum IL-6 concentration. The following table shows mouse bacterial load in blood after infection.

|  | Number of Mice Bled | CFU/ml |
|---|---|---|
| Control* | 6 | 0, 0, $3.6 \times 10^3$, $1.6 \times 10^3$, $4.6 \times 10^5$, $>10^5$ |
| PNA [10 µM] | 4 | 0, 0, 0, 0 |
| IP, PNA [100 µM] | 4 | 0, 0, 0, 0 |

*Septicemic mice succumbed to infection prior to 46 h.

Serum sample was collected at 24 hrs after infection for cell growth assay by measuring viable cell count. Viable cell count was done by diluting the cultures and plating on LB plates. Plates were incubated overnight at 37° C. and the number of colonies enumerated by visual inspection.

Inhibition of Bacterial Growth by ODN.

Figure 14:
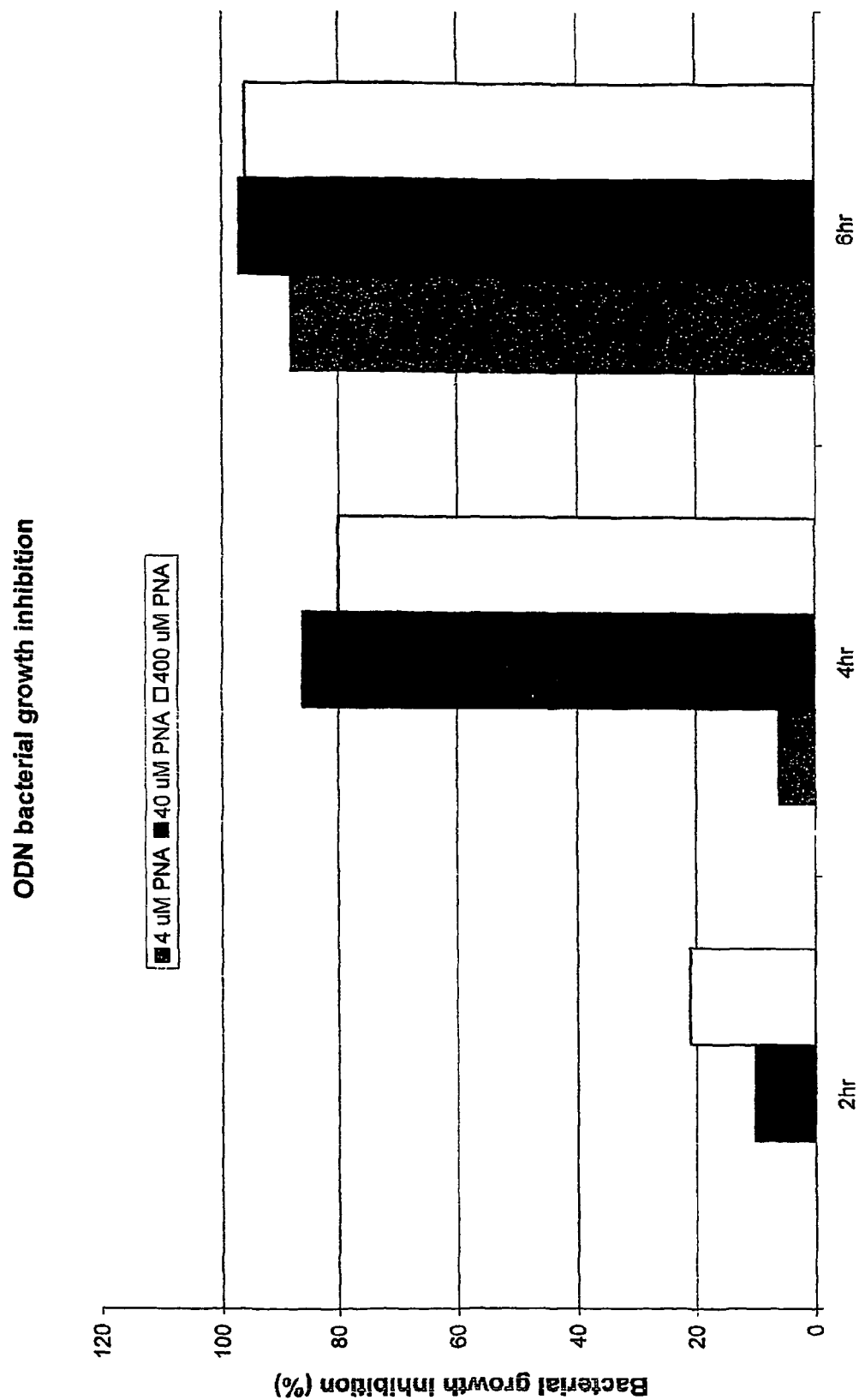

The inhibition of bacterial growth by ODN was evaluated by examining the effect of ODN dosage on SM101 growth. In this study, an ODN having the sequence CTC ATA CTC T was added to the 1/50 diluted O/N SM101 cell cultures, at final concentration of 40 µM or 400 µK with addition of equal volume water as a negative control, and incubated with shaking at 30° C. After 2, 4 or 6 h, the growth was measured by either the optical density at 600 nm (OD600) or viable cell count, which was done by diluting the cultures and plating them in triplicate on LB plates with streptomycin. As shown in FIG. 14, upon addition of ODN, cell growth was inhibited by 86-96%.

Inhibition of Bacterial Growth by ODN Expression Plasmid.

Figure 15:
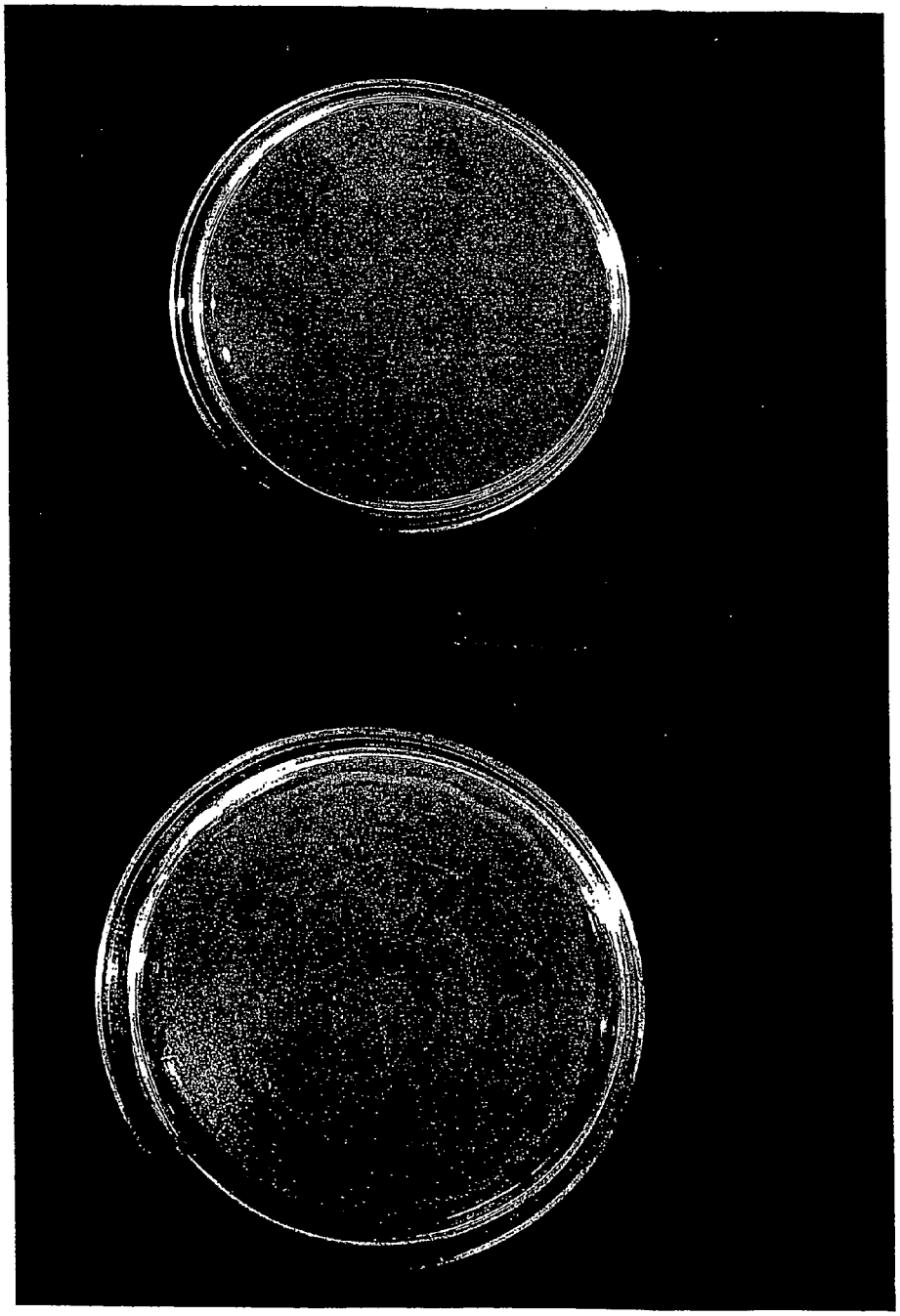
FIG. 15 shows bacterial growth inhibition in competent XL10-gold(kan) cells transformed with ODN expression plasmid AS830103 or the plasmid without ODN insert plated onto LB media with chloramphenicol and incubated at 37° C. O/N.

In this study, the ODN expression plasmid As080103, having the sequence CYGX080103 listed above, and plasmid pssxGb without ODN insert as negative control, were transformed into E. coli XL10-goldokan). The resulting cell cultures were plated on LB media with chloramphenicol and incubated at 37° C. O/N. As shown in FIG. 15, no XL10-gold (kan) carrying ODN expression plasmid grew on the LB media.

Establishing Lethal Dose (LD70) in the Mouse Model.

Six-week-old mice Balb/c (in groups of five) were used for infection experiments. A serial dilution of SM101 was injected intraperitoneally (i.p.) into mice in 400 µl aliquots. The animals were observed for 100 h. Mice inoculated with bacteria were scored for their state of health on a scale of 5 to 0 based on progressive disease states reflected by several clinical signs. A normal and unremarkable condition was scored as 5; slight illness, defined as lethargy and ruffled fur, was scored as 4; moderate illness, defined as severe lethargy, ruffled fur, and hunched back, was scored as 3; severe illness, with the above signs plus exudative accumulation around partially closed eyes, was scored as 2; a moribund state was scored as 1; and death was scored as 0. While experiments were not conducted in a double-blind manner all animals were evaluated by two or more independent observers. These experiments established that $10^9$ CFUT of strain SM101 is the LD70 for 6 week-old mice Balb/c, with ~60% mice that received the LD70 dose dying within 48 h. This LD70 was used in the DNA therapy experiments described infra. A similar approach was used to establish the UD70 for E. coli strain K-12.

Treatment of Sepsis Using ODN.

The efficacy of ODN therapy was evaluated in two experiments using the above-described SM101 bacteremia mouse model. The first examined the effect of DNA dose on the ability of ODN to rescue mice from SM101 bacteremia. The second studied the effect on the outcome of delaying treatment for various periods. In the dose-ranging study, five groups of mice (five mice in each) were challenged by i.p. injection of the LD70 of SM101. Each group was treated with a single injection of the ODN CTC ATA CTC T,    [Seq. ID No. 33]

administered i.p. immediately after the bacterial challenge at 4 nmol, 40 nmol, 400 mmol and 0 nmol. As an additional control, a fifth group (two mice) was not challenged with bacteria, receiving only the injection of ODN (at the highest dose). The state of the health of these animals was monitored for one week. FIG. 12 shows survival of infected mice with or without ODN treatment.

Delivering Plasmid to Target Bacterial Cells by Bacteriophage T3 Extracts.

A standard DNA packaging reaction mixture (25 µl) contains 0.5 mg plasmid DNA, $2 \times 10^{10}$ phage equivalent(peg) of prohead, 20 pmol of gp 18 and 3 pmol of gp 19 in complete pac buffer. The reaction mixture was incubated at 30° C. for 30 min for DNA packaging and the reaction was terminated by the addition of 1 µl of 2 mg/ml of DNaseI. After incubation at 30° C. for 20 min, the filled heads were converted to infectious particles by incubation with a head acceptor extract containing tail and tail fiber proteins. Proheads were prepared through a sucrose gradient centrifuge of lysates of bacterial cells infected with bacteriophage T3, as described by Nakasu, et al. (1983, Virology, 127, 124-133). gp 18 and gp 19 proteins were purified as decribed by Hamada, et al. (1986, Virology, 151, 110-118). The head acceptor extracts were isolated from lysates of bacterial cells infected by bacteriophage T3 and purified through ammonium sulfate precipitation. The resulting infectious particles contain the ODN expression plasmid for delivery to the target bacterial cells.

Inhibition of Bacterial Growth by Peptide-ODN Conjugate.

Figure 16:
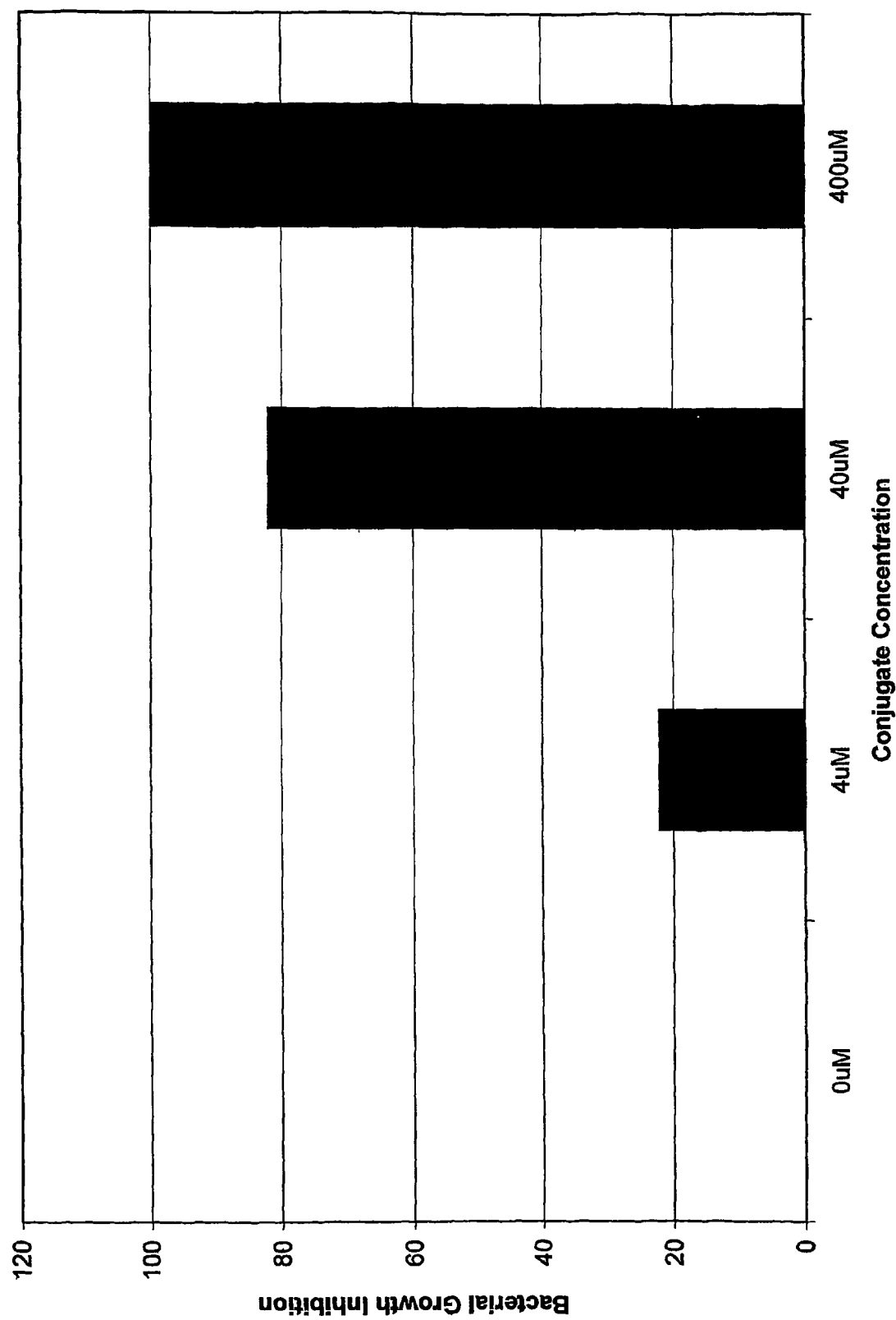
FIG. 16 shows dose-dependent inhibition of bacterial growth by a peptide-PNA conjugate. As shown, the conjugate inhibited K-12 cell growth by 82-99.8%.

The inhibition of bacterial growth by peptide-PNA conjugate was evaluated by examining the effect of conjugate dose on the ability of conjugate to inhibit K12 growth. In this study, a peptide-ODN conjugate having the sequence KFFKFFKFFK-CTC ATA CTC T    [Seq. ID No. 34]

was added to the 1/50 diluted O/N K12 cell cultures, and final concentration of 4 µM, 40 µM, or 400 µM, with addition of equal volume water as a negative control, and incubated with shaking at 37° C. Immediately after, diluting the O/N culture ⅟₅₀, peptide-ODN conjugate was added to final concentration of 4 µM, 40 µM, or 400 µK, with addition of equal volume water as a negative control, and incubated with shaking at 37° C. After 2 hours, growth was measured by viable cell count by diluting the cultures and plating in triplicate on LB plates. As shown in FIG. 16, upon addition of peptide-ODN conjugate, cell growth was inhibited by 82-99.8%.

Reduction of Mouse Bacterial Load in Blood by Peptide-ODN Conjugate.

The efficacy of peptide-ODN conjugate therapy was evaluated by examining the ability of the conjugate to reduce mouse bacterial load in blood. In this study, the log-phase preparation of K12 was diluted in PBS and six-week old mice Balb/c were infected by i.p. injection of $3 \times 10^9$ CFU wild-type bacteria K12. The infected mice were treated with a single injection of 50 nmol peptide-ODN conjugate [Seq. ID No. 34], administered i.p. 30 min after the bacterial challenge. The conjugate was either mixed with bacteria in vitro and then injected in mice or mice were prost-treated by conjugate 30 min after infection. Serum samples were collected, at 24 hrs after infection, for cell growth assay by measuring viable cell count. Viable cell count was done by diluting the cultures and plating them on LB plates. The results are shown in the following table:

|  | Number of Mice Bled | CFU/ml |
| --- | --- | --- |
| Control* | 3 | $1.3 \times 10^6$, $1.4 \times 10^5$, $1.3 \times 10^5$ |
| PNA [10 µM] | 4 | $5.1 \times 10^4$, $9.4 \times 10^4$, $7.0 \times 10^5$, $1.5 \times 10^4$ |
| IP, PNA [100 µM] | 4 | $2.1 \times 10^4$, $1.1 \times 10^5$, $6.8 \times 10^4$, 160 |

The present invention relates to a new strategy for combating bacterial and fungal pathogens, wherein selected ODNs and the expression plasmid used to produce them are used as therapeutic agents. One such pathogenic condition that is treated successfully utilizing the ODNs and expression plasmids of the present invention is sepsis. Examples of sepsis-causing microorganisms that can be treated in accordance with the present invention include, but are not limited to, those that cause infections in the lung, abdomen, bloodstream, skin, soft tissue, infections associated with intravascular devices, sand respiratory infections. Examples of other pathogenic microorganisms that can be treated in accordance with the present invention include, but are not limited to, Gram-negative bacteria such as *Bacteroides, Fusobacterium, Escherichia, Klebsiella, Salmonella, Shigella, Proteus, Pseudomonas, Vibrio, Legionella, Haemophilus, Bordetella, Brucella, Campylobacter, Neisseria, Branhamella*; Gram-positive bacteria such as *Streptococcus, Staphylococcus, Peptococcus, Bacillus, Listeria, Clostridium*, Propionebactaria; organisms that stain poorly or not at all with Gram's stain such as *Mycobacteria, Treponema, Leptospira, Borrelia, Mycoplasma, Clamydia, Rickettsia* and *Coxiella*; and fungi such as *Candida*, Aspergillosis, Blastomycdsis, Coccidioidomycosis, Cryptococcosis, Histoplasmosis, Paracoccidiomycosis, Sporotrichosis, Zygomycosis.

Examples of bacterial target genes that can be knocked down in accordance with the present invention include, but are not limited to, those identified from library screening and those chosen based upon knowledge of bacterial physiology. A target gene can be found among those involved in one of the major process complexes: cell division, cell wall synthesis, protein synthesis (translation), nucleic acid synthesis, fatty acid metabolism, and gene regulation. Therefore, examples of bacterial target genes that can be knocked down in accordance with the present invention include, but are not limited to the above-described FtsZ gene, MurB, acpP, 16s rRNA, PBPs, DNAA, DNAC, pcrA, rpoB, rpoA, rpoC, rpsC, rpsD, rpsF, rpsI, rpsJ, rpsM, rpsR, FabK, FabH, rplB, rplC, rpU, rplK, rplM, rplN, rplO, rplP; rplR, rplT, rplV, rplX, rpmA, rpmL. valS, serS, proS, cysS, alaS, pheS, sporC, tsf, tufA, fus, secA, secV, pyrC.

The target genes critical to fungal viability can be found among those involved in one of the major process complexes: cell division, cell wall synthesis, protein synthesis (translation), nucleic acid synthesis, fatty acid metabolism, and gene regulation. Therefore, examples of fungal target genes that can be knocked down in accordance with the present invention include, but are not limited to, ERG1, ERG2, ERG3, ERG4, ERG5, ERG6, ERG7, ERG11, ERG24, ERG25, ERGX, ERGY, CHS1, CHS2, CHS3, CWP1, CWP2, KRE1, KRE2, KRE5, KRE11, TIP1, GFA1.

ODN technology can down-regulate the over-expression of the host genes associated with the exaggerated innate immune response in sepsis, so that appropriate, host response to an infection remains. Examples of host target genes that can be knocked down in accordance with the present invention include, but are not limited to, tumor necrosis factor (TNF), interleukin-1 (IL-1), interleukin-6 (16), interleukin-12 (IL-12), interleukin-15 (IL15), nitric oxide synthase (NOS), high mobility group I protein HMG-1), migration inhibitory factor, kinins, platelet-activating factor receptor antagonist (PAFra), soluble phospholipase A2 (sPLA2). In particular, TNF is considered to be one of the most important inflammatory mediators in the sepsis cascade. TNF is significantly elevated during sepsis (Casey, et al., 1993, Ann. Intern. Med. 119:771-778; van der Poll, et al., 1995, Shock, 1-12), and levels of TNF have been associated with severity of sepsis and clinical outcome (Calandra, et al., 1990, J. Infect. Dis. 161:982-987; Cannon, et al., 1990, J. Infect. Dis., 161:79-84). Moreover, most of the deleterious effects of sepsis can be mimicked by the administration of TNF (Okusawa, et al., 1988, J. Clin. Invest., 81:1162-1172; Natanson, et al., 1989, J. Exp. Med., 169:823-832).

Examples of the ODN therapeutics that are used to treat sepsis in accordance with the present invention include, but are not limited to, CYGX080103, wherein, its sequence is 5'(CTT TCA ACA GTT TTG ATG ACG TTT GCT GAC CAT ACA ATT GCG ATA TCG TGG GGA GTG AGA G)3', and its potential targets are btuE (GenBank ID: NP_416225.1), CaiB (GenBank ID: NP_414580.1), ydgD (GenBank ID: NP_418152.1), ygcQ (GenBank ED: NP_417249.2), ftsH (GenBank ID: NP_417645.1), ppiB (GenBank ID: NP_415058.1), yihI (GenBank ID: NP_418308.1), zntA (GenBank ID: NP_417926.1), yicI (GenBank ID: NP_418116.1), fhuA (GenBank ID: NP_414692.1), rplD (GenBank BD: NP_417778.1), ilvB (GenBank ID: NP_418127.1), lepB (GenBank ID: NP_417063.1), aroK (GenBank ID: NP_417849.1), mfd (GenBank ID: NP_415632.1), rlpA (GenBank ID: NP_415166.1), accA (GenBank ID: NP_414727.1), pgpA (GenBank ID: NP_414952.1); CYGXacpP, wherein, its sequence is 5'(CTC ATA CTC T)3' in PNA form, and its target is the bacterial essential fatty acid biosynthesis gene acpP (GenBank ID: NP_309499); CYGXFtsZDZ, wherein, its sequence is 5'(GTT TCG AAG GCT AGC TAC AAC GAT CAT CCA G)3', and its target is the bacterial essential cell division gene FtsZ (Gendank ID: NP_308126).

Examples of the DNA therapeutics that are used to treat sepsis in accordance with the present invention include, but are not limited to, regular ODN and its expression plasmid, its modification forms such as locked nucleic acids (LNA), peptide nucleic acids (PNA) such as those described above, phosphorothioates, or phosphorothioates morpholino oligomer (PMO).

Examples of means for delivering the ODNs and the said ODN expression plasmids of the present invention into bacterial or fungal cells for treatment of bacterial or fungal pathogenic conditions in accordance with the present invention include, but are not limited to, direct injection of naked DNA; cationic polymers such as PEI, EPEI, and porphyrins; viral vectors such as retroviruses and adenoviruses; cationic liposomes such as DOTAP and DOTMA; and peptides such as Xaa Xaa Xaa Lys Lys Arg Arg Xaa Xaa Xaa Xaa Xaa Xaa Thr Trp Xaa Glu Thr Trp Trp Xaa Xaa Xaa, Lys Xaa Xaa Trp Trp Glu Thr Trp Trp Xaa Xaa Ser Gin Pro Lys Lys Xaa Arg Lys Xaa, Tyr Gly Phe Lys Lys Xaa Arg Arg Pro Tip Thr Trp Trp Glu Thr Trp Trp Thr Glu Xaa, wherein any Xaa can be any amino acid. The ODN expression plasmids of the present invention are also delivered into bacterial or fungal cells by packaging the plasmids-into infectious particles using phage extracts as detailed above.

The anti-fungal sequences (AFS) and anti-bacterial sequences (ABS) of the present invention can be incorporated into plasmids, viral, and other vectors as known in the art and packaged in liposomes, cationic polymers such as PEL or other excipient(s) and used, for instance, prophylactically to prevent or reduce the likelihood of infections such as the infections that lead to sepsis. Such uses include, but are not limited to, sprayed applications on the skin or onto the site of surgical incisions to reduce bacterial loads and thus to reduce the risk of infection. The AFS and ABS of the present invention are also used to advantage in this same manner against local infections and by systemic infusion intravenously. A "cocktail" of AFS and ABS for common microbial pathogens is administered for this purpose or, once the bacterial or fungal pathogen is cultured and identified, the appropriate sequence(s) for the specific pathogen are chosen and administered.

The AFS and ABS of the present invention are also used in conjunction with sequences against a host's inflammation related proteins such as the Intercellular Adhesion Molecule (ICAM) in the manner described in International Application No. PCT/US02/12345, assigned to the same Assignee of the present invention. Combined use of the anti-inflammatory and anti-bacterial sequences can reduce the risk of infection and scarring from surgical procedures. The combined sequences are also useful as a treatment for inflammatory conditions that lead to infections such as decubiti (bed sores).

Those skilled in the art who have the benefit of this disclosure will recognize that certain changes can be made to the component parts of the apparatus of the present invention without changing the manner in which those parts function to achieve their intended result. All such changes, and others that will be clear to those skilled in the art from this description of the invention, are intended to fall within the scope of the following, non-limiting claims.

What is claimed is:

1. A vector for expressing a single-stranded oligonucleotide in a bacterial or fungal cell, comprising: a promoter; a set of inverted tandem repeats located 3' to the promoter; a cloning site flanked by the set of inverted tandem repeats or located 3' to the set of inverted tandem repeats; a primer binding site (PBS) for a reverse transcriptase located 3' to the cloning site; and an expression termination sequence located 3' to the PBS and wherein the primer binding site (PBS) has a sequence: TGGTGCGTCCGAG [SEQ ID NO: 3].

2. The cloning vector according to claim 1, further comprising a gene coding for the reverse transcriptase.

3. The vector according to claim 2, wherein the reverse transcriptase is a mouse Maloney virus reverse transcriptase.

4. The vector according to claim 1, further comprising an origin of replication.

5. The vector according to claim 1, wherein the promoter is a bacterial promoter.

6. The vector according to claim 1, wherein the promoter is inducible.

7. The vector according to claim 6, wherein the promoter is inducible by tetracycline or a tetracycline analog.

8. The vector according to claim 1, wherein the vector is pssXG.

9. The vector according to claim 1, further comprising an oligonucleotide insert inserted at the cloning site.

10. A library for expressing single-stranded oligodeoxynucleotides, comprising a plurality of vectors according to claim 9, wherein the oligonucleotide inserts in the plurality of vectors have different nucleotide sequences.

11. The library according to claim 10, wherein the oligonucleotide inserts have sequences of: 5'-N.sub.I-GGCTAGC-TACAACGA-N.sub.2[SEQ ID NO: 7], wherein N.sub.1 and N.sub.2 each represent a nucleotide sequence having a random sequence and a length from 3 to 25 nucleotides long.

12. A cell having a vector according to claim 1.

13. A method for screening an oligodeoxynucleotide that modulates a cell function using the library of claim 10, wherein the promoter in the vector is inducible, the method comprising: transfecting the library into host cells; growing the transfected host cells on replica plates, one of the replica plates including an agent for inducing expression of single-stranded oligodeoxynucleotides from the oligonucleotide inserts in the vectors in the transfected host cells; comparing the induced and non-induced replica plates to identify a host cell having a different phenotype; and sequencing the oligonucleotide insert in the vector from the host cell having a different phenotype.

14. The vector of claim 9, wherein the oligonucleotide insert is determined to have a sequence of: 5'-CTTTCAA-CAGTTTTGATGACCTTTGCTGACC [SEQ ID NO: 14] ATACAATTGCGATATCGTGGGGAGTGAGAG-3', 5'-CT-CATACTCT-3', [SEQ ID NO: 33] 5'-GTTTCGAAG-GCTAGCTACAACGATCATCCA [SEQ ID NO: 6], or 5'-CCTGCTTAGGCTAGCTACAACGATGGTCAC [SEQ ID NO: 8].

15. A cell having the vector according to claim 14 transfected.

16. A method for inhibiting bacterial, fungal or other microbial growth or reducing toxin activity, comprising contacting bacteria, fungi or other microorganism with the vector of claim 14.

17. A method for inhibiting bacterial, fungal or other microbial growth or reducing toxin activity, comprising contacting bacteria, fungi or other microorganism with the vector of claim 9.

18. The method of claim 16, wherein the bacteria, fungi or other microorganism is a sepsis causative agent.

19. A method for reducing or blocking sepsis-related toxin activity or sepsis-induced immune responses, comprising contacting a bodily fluid with the vector of claims 9.

* * * * *

SEQUENCE LISTING

```
<160> NUMBER OF SEQ ID NOS: 39

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ctagctagct agcgatcgat gggaccaatg gggcag                                    36

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cggggtacca gtattccctg gtc                                                  23

<210> SEQ ID NO 3
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tggtgcgtcc gag                                                             13
```

```
<210> SEQ ID NO 4
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
taactggatg atcgttgtag ctagccttcg aaacttggtg gtgcgtccga gtggaccggg      60
agacccctgc tcgagt                                                     76

<210> SEQ ID NO 5
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ctagactcga gcaggggtct cccggtccac tcggacgcac caccaagttt cgaaggctag      60
ctacaacgat catccagtta at                                              82

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gtttcgaagg ctagctacaa cgatcatcca g                                    31

<210> SEQ ID NO 7
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(25)
<223> OTHER INFORMATION: This region may encompass 3 to 25 variable
      nucleotides, and preferably 7 to 10 nucleotides;
      a, c, g, or t.
<220> FEATURE:
<221> NAME/KEY: modified_base
<222> LOCATION: (41)..(65)
<223> OTHER INFORMATION: This region may encompass 3 to 25 variable
      nucleotides, and preferably 7 to 10 nucleotides;
      a, c, g, or t.

<400> SEQUENCE: 7
nnnnnnnnnn nnnnnnnnnn nnnnnggcta gctacaacga nnnnnnnnnn nnnnnnnnnn      60 nnnnn                                                                 65

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 8
cctgcttagg ctagctacaa cgatggtcac c                              31

<210> SEQ ID NO 9
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(50)
<223> OTHER INFORMATION: a, c, g, or t

<400> SEQUENCE: 9
ctctcactcc nnnnnnnnnn nnnnnnnnnn nnnnnnnnnn nnnnnnnnnn actgttgaaa     60
ggc                                                                  63

<210> SEQ ID NO 10
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
cggagagtga gg                                                        12

<210> SEQ ID NO 11
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ctttcaacag t                                                         11

<210> SEQ ID NO 12
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(20)
<223> OTHER INFORMATION: a, c, g, or t
<220> FEATURE:
<221> NAME/KEY: modified_base
<222> LOCATION: (36)..(43)
<223> OTHER INFORMATION: a, c, g, or t

<400> SEQUENCE: 12
ctcgagtcta gannnnnnnn ggctagctac aacgannnnn nnnttaatta agctagc        57

<210> SEQ ID NO 13
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 13
gctagcttaa ttaa                                              14

<210> SEQ ID NO 14
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ctttcaacag ttttgatgac ctttgctgac catacaattg cgatatcgtg gggagtgaga    60
g                                                             61

<210> SEQ ID NO 15
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cctttgctga ccatac                                            16

<210> SEQ ID NO 16
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gacctttgct gacca                                             15

<210> SEQ ID NO 17
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
acagttttga tgac                                              14

<210> SEQ ID NO 18
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
acaattgcga tat                                               13

<210> SEQ ID NO 19
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 19
gacctttgct gac                                                        13

<210> SEQ ID NO 20
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tcaacagttt tgatgac                                                    17

<210> SEQ ID NO 21
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
atgacctttg ctg                                                        13

<210> SEQ ID NO 22
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cagttttgat ga                                                         12

<210> SEQ ID NO 23
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
acctttgctg ac                                                         12

<210> SEQ ID NO 24
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ttgctgacca ta                                                         12

<210> SEQ ID NO 25
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 25
tgacctttgc tg                                                          12

<210> SEQ ID NO 26
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gttttgatga cc                                                          12

<210> SEQ ID NO 27
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gcgatatcgt gg                                                          12

<210> SEQ ID NO 28
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ttgatgacct tt                                                          12

<210> SEQ ID NO 29
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tggggagtga g                                                           11

<210> SEQ ID NO 30
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ttgctgacca t                                                           11

<210> SEQ ID NO 31
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
```
ttttgatgac c                                                                                    11

<210> SEQ ID NO 32
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
tgatgacctt t                                                                                    11

<210> SEQ ID NO 33
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ctcatactct                                                                                      10

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Lys Phe Phe Lys Phe Phe Lys Phe Phe Lys
 1               5                  10

<210> SEQ ID NO 35
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Variable amino acid
<220> FEATURE:
<221> NAME/KEY: MOD_RES
<222> LOCATION: (8)..(13)
<223> OTHER INFORMATION: Variable amino acid
<220> FEATURE:
<221> NAME/KEY: MOD_RES
<222> LOCATION: (16)
<223> OTHER INFORMATION: Variable amino acid
<220> FEATURE:
<221> NAME/KEY: MOD_RES
<222> LOCATION: (21)..(23)
<223> OTHER INFORMATION: Variable amino acid

<400> SEQUENCE: 35

Xaa Xaa Xaa Lys Lys Arg Arg Xaa Xaa Xaa Xaa Xaa Xaa Thr Trp Xaa
 1               5                  10                  15

Glu Thr Trp Trp Xaa Xaa Xaa
                20

<210> SEQ ID NO 36
<211> LENGTH: 20

```
-continued

<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (10)..(11)
<223> OTHER INFORMATION: Variable amino acid
<220> FEATURE:
<221> NAME/KEY: MOD_RES
<222> LOCATION: (17)
<223> OTHER INFORMATION: Variable amino acid
<220> FEATURE:
<221> NAME/KEY: MOD_RES
<222> LOCATION: (20)
<223> OTHER INFORMATION: Variable amino acid

<400> SEQUENCE: 36

Lys Xaa Xaa Trp Trp Glu Thr Trp Trp Xaa Xaa Ser Gln Pro Lys Lys
 1               5                  10                  15

Xaa Arg Lys Xaa
            20

<210> SEQ ID NO 37
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: Variable amino acid
<220> FEATURE:
<221> NAME/KEY: MOD_RES
<222> LOCATION: (20)
<223> OTHER INFORMATION: Variable amino acid

<400> SEQUENCE: 37

Tyr Gly Phe Lys Lys Xaa Arg Arg Pro Trp Thr Trp Trp Glu Thr Trp
 1               5                  10                  15

Trp Thr Glu Xaa
            20

<210> SEQ ID NO 38
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
auggcaaagc uugaguaggu cugc                                              24

<210> SEQ ID NO 39
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      6xHN tag

<400> SEQUENCE: 39

His Asn His Asn His Asn His Asn His Asn His Asn
 1               5                  10
```